US011744961B2

(12) United States Patent
Pelkus

(10) Patent No.: US 11,744,961 B2
(45) Date of Patent: Sep. 5, 2023

(54) PORTABLE MEDICAL TREATMENT SYSTEM AND METHOD OF USE

(71) Applicant: Vaporox, Inc., Denver, CO (US)

(72) Inventor: Adrian Pelkus, San Marcos, CA (US)

(73) Assignee: VAPOROX, INC., Denver, CO (US)

(*) Notice: Subject to any disclaimer, the term of this patent is extended or adjusted under 35 U.S.C. 154(b) by 725 days.

(21) Appl. No.: 16/505,391

(22) Filed: Jul. 8, 2019

(65) Prior Publication Data

US 2020/0101241 A1    Apr. 2, 2020

Related U.S. Application Data

(63) Continuation of application No. 15/312,156, filed as application No. PCT/US2015/018856 on Mar. 5, 2015, now Pat. No. 10,342,933.

(Continued)

(51) Int. Cl.
*A61M 35/00* (2006.01)
*A61H 35/00* (2006.01)
(Continued)

(52) U.S. Cl.
CPC .......... *A61M 11/005* (2013.01); *A61M 35/00* (2013.01); *A61M 35/10* (2019.05);
(Continued)

(58) Field of Classification Search
CPC ..... A61H 35/00; A61H 35/006; A61M 35/00; A61M 37/00; A61N 5/0613
See application file for complete search history.

(56) References Cited

U.S. PATENT DOCUMENTS 3,101,716 A   8/1963 Cornell, Jr.
3,744,491 A   7/1973 Fischer
(Continued)

FOREIGN PATENT DOCUMENTS

CA   2032263    1/1990
CA   2 528 965   11/2004
(Continued)

OTHER PUBLICATIONS

International Search Report dated May 8, 2008, issued in International Appl. No.: PCT/US06/28799 (002 Series).
(Continued)

*Primary Examiner* — Catharine L Anderson
(74) *Attorney, Agent, or Firm* — Knobbe Martens Olson & Bear LLP

(57) ABSTRACT

A medical treatment system including a treatment chamber, a source of an aqueous mist containing a medication, a source of an oxygen-enriched gas, and a control system adapted to alternately surround a human body part with a mist containing a medication and the oxygen enriched gas, which can be used to treat various skin disorders including infected lesions, bacterial infections such as acne (i.e. *Propionibacterium acnes*), fungal infections such as Athlete's foot (i.e. fungal genus *Trichophyton*), conditions associated with hair loss including alopecia as well as ulcerations and frostbite resulting from poor circulation. A method of treating skin disorders is also disclosed, that includes providing a mist containing a medication and enriched oxygen gas to the site being treated as well as providing oxygen to the patient during treatment.

17 Claims, 2 Drawing Sheets

Related U.S. Application Data

(60) Provisional application No. 61/955,642, filed on Mar. 19, 2014.

(51) Int. Cl.
    *A61M 11/00*         (2006.01)
    *A61M 37/00*         (2006.01)
    *A61M 39/22*         (2006.01)
    *A61N 5/06*          (2006.01)
    A61F 17/00          (2006.01)
    A61F 13/00          (2006.01)

(52) U.S. Cl.
    CPC ............ *A61M 37/00* (2013.01); *A61M 39/22* (2013.01); *A61N 5/0613* (2013.01); *A61F 13/00051* (2013.01); *A61F 17/00* (2013.01); *A61M 2205/33* (2013.01); *A61N 2005/0651* (2013.01); *A61N 2005/0659* (2013.01); *A61N 2005/0661* (2013.01)

(56) References Cited

U.S. PATENT DOCUMENTS

| | | | |
|---|---|---|---|
| 4,236,513 A | 12/1980 | LoPiano | |
| 4,331,137 A | 5/1982 | Sarui | |
| 4,432,354 A * | 2/1984 | Lasley | A61G 10/026 601/43 |
| 4,670,010 A | 6/1987 | Dragone | |
| 4,772,259 A | 9/1988 | Frech et al. | |
| 5,098,415 A | 3/1992 | Levin | |
| 5,188,099 A | 2/1993 | Todeschini | |
| 5,228,431 A | 7/1993 | Giarretto | |
| 5,312,385 A | 5/1994 | Greco | |
| 5,447,504 A | 9/1995 | Baker et al. | |
| 5,848,998 A | 12/1998 | Marasco, Jr. | |
| 6,273,906 B1 | 8/2001 | Swanson | |
| 6,443,978 B1 | 9/2002 | Zharov | |
| 6,868,851 B2 | 3/2005 | Heinonen | |
| 7,665,460 B2 | 2/2010 | Lindsay et al. | |
| 7,771,402 B2 | 8/2010 | Marasco | |
| 7,934,703 B2 | 5/2011 | Tomono et al. | |
| 8,048,044 B2 | 11/2011 | Stryker et al. | |
| 8,241,258 B2 * | 8/2012 | Pelkus | A61G 10/02 604/289 |
| 8,353,882 B1 | 1/2013 | Pelkus | |
| 8,440,221 B2 * | 5/2013 | Zumbrunn | A61M 35/00 424/449 |
| 8,499,764 B2 | 8/2013 | Hills et al. | |
| 9,004,065 B2 * | 4/2015 | Vervoort | A61M 16/022 128/204.23 |
| 10,004,914 B2 * | 6/2018 | Nettesheim | A61L 2/0011 |
| 11,090,475 B2 * | 8/2021 | Pelkus | A61H 35/006 |
| 2003/0023283 A1 | 1/2003 | McDaniel | |
| 2004/0260253 A1 | 12/2004 | Rosati | |
| 2005/0107766 A1 | 5/2005 | Ott et al. | |
| 2006/0069357 A1 | 3/2006 | Marasco | |
| 2007/0286809 A1 | 12/2007 | Williams et al. | |
| 2008/0091179 A1 | 4/2008 | Durkin et al. | |
| 2009/0048555 A1 | 2/2009 | Stryker et al. | |
| 2009/0112170 A1 | 4/2009 | Wells | |
| 2009/0234270 A1 | 9/2009 | Loebel et al. | |
| 2010/0001096 A1 | 1/2010 | Lu | |
| 2010/0022941 A1 | 1/2010 | Pelkus | |
| 2010/0150991 A1 | 6/2010 | Bernstein | |
| 2010/0219263 A1 | 9/2010 | Feriani et al. | |
| 2011/0061479 A1 | 5/2011 | Burt et al. | |
| 2012/0022436 A1 | 1/2012 | Bradley | |
| 2012/0071813 A1 | 3/2012 | Schaefer | |
| 2012/0138050 A1 | 6/2012 | Wondka et al. | |
| 2012/0302976 A1 | 11/2012 | Locke et al. | |
| 2016/0256637 A1 | 9/2016 | Kern | |
| 2016/0354559 A1 | 12/2016 | Gavini et al. | |
| 2017/0232211 A1 | 8/2017 | Gallem et al. | |
| 2017/0361345 A1 | 12/2017 | Maeda et al. | |
| 2017/0368270 A1 | 12/2017 | Kinoshita et al. | |
| 2018/0066645 A1 | 3/2018 | Mazur | |
| 2020/0101241 A1 | 4/2020 | Pelkus | |

FOREIGN PATENT DOCUMENTS

| | | |
|---|---|---|
| CN | 1788709 A | 6/2006 |
| CN | 201171784 Y | 12/2008 |
| WO | WO 2008/013524 A2 | 1/2008 |
| WO | WO 2014/092802 | 6/2014 |

OTHER PUBLICATIONS

Extended/Supplementary European Search Report for EP Application No. 13861708.9 dated May 2, 2017.

International Search Report for International Application No. PCT/US2013/048801 dated Jan. 31, 2014.

International Search Report for International Application No. PCT/US15/18856 dated May 27, 2015.

Supplementary European Search Report for Application No. EP 15 76 4163 dated Jan. 17, 2018.

Office Action received in related Chinese Application No. 201580027022.X dated Apr. 1, 2019.

International Search Report for PCT Application No. PCT/US21/59481 dated Feb. 3, 2022.

* cited by examiner

PORTABLE MEDICAL TREATMENT SYSTEM AND METHOD OF USE

RELATED APPLICATIONS

The present application is a continuation of U.S. patent application Ser. No. 15/312,156, filed Nov. 17, 2016, which is a U.S. National Phase Application of PCT/US2015/018856, filed Mar. 5, 2015, which claims priority to U.S. Provisional Application No. 61/955,642, filed Mar. 19, 2014. Any and all applications for which a foreign or domestic priority claim is identified in the Application Data Sheet as filed with the present application are hereby incorporated by reference under 37 CFR 1.57.

TECHNICAL FIELD

The present disclosure relates in general to portable medical treatment systems. More particularly, the present disclosure relates to a medical treatment apparatus that can be easily transported by a patient or set up on a table top and used to treat a variety of medical conditions including surface wounds such as minor cuts and abrasions, deep wounds extending below the dermis such as cuts resulting from accidental injury or from surgery including healing wounds resulting from amputations or plastic surgery, medical conditions such as bacterial or fungal infections including acne or Athlete's foot, ulcerations that have difficulty healing because of diabetes, pressure soars resulting from a physical condition where a patient is bed ridden or confined to a wheelchair, burns or frostbite.

BACKGROUND

Medical professionals and healthcare providers such as nurses and doctors routinely treat patients having various skin disorders including lacerations, abrasions, surgical incision, infected lesions, bacterial infections such as acne (i.e. *Propionibacterium acnes*), fungal infections such as Athlete's foot (i.e. fungal genus *Trichophyton*), conditions associated with hair loss including alopecia areata (patch baldness), alopecia totalis (complete baldness of the scalp) and alopecia universalis (body baldness) as well as ulcerations from systemic conditions such as diabetes, frostbite and burns. Variations in skin disorders and other patient indications dictate variations in desired medications for treatment, such as antibiotics, growth factors, enzymes, hormones, as well as protocols, such as delivery rates for medication and creating and maintaining an antiseptic environment.

The skin is a barrier and a first line of defense from external factors in the environment. It also functions to prevent excessive water loss, provide insulation, temperature regulation and sensation. When the skin is damaged or broken this protection is compromised subjecting the body to invasion by potential pathogens. Consequently, repairing or providing an environment in which the skin can repair itself is crucial for survival. Current treatment for skin lacerations and scrapes includes cleaning the site thoroughly with soap and water and keeping the wound clean and dry. The use of antibiotic ointments or hydrogen peroxide may also be used to reduce the possibility of infection. However, compliance with this protocol can be difficult to achieve for the length of time necessary to heal the wound. Consequently, when the area affected becomes red, swollen, and painful to the touch this generally indicates infection. Over a hundred thousand people die each year in hospitals from infections resulting from open wounds, several thousand loose limbs and still others are disfigured by scars left after the wound has healed.

A vast majority of bacteria are harmless or beneficial. However, there are a few that are pathogenic. One such bacterium, *Propionibacterium acnes* causes acne vulgaris, seborrhea (scaly red skin), comedone (blackheads and whiteheads) and pimples often resulting in scarring and in extreme cases disfigurement. It is estimated that nearly 85% of people between the ages of 12 to 24 develop acne. Young men are more likely to suffer the effects of acne for longer periods of time then young women because testosterone tends to make acne worse. In 2013, it was estimated that there were over 316 million people in the United States and approximately one third of those individuals were between the ages of 10 and 24. With close to 100 million suffering from acne in the United States (U.S.) alone the skin care industry for the past fifty or so years has been developing treatments but with limited success. Currently, most medications include one or more of the following chemicals: benzoyl peroxide, salicylic acid, glycolic acid, sulfur and azelaic acid. However, because most individual's skin is unique, it is difficult to find the appropriate formulation that will relieve or eliminate acne. Consequently, many individuals do not obtain proper treatment and are left to suffer with acne and often have scaring as a result. The need for effective treatment is evidenced by individuals spending over 78 billion dollars on skin care worldwide in 2010 with facial care capturing 64% of this market.

Athlete's foot also known as Tinea pedis is an inflammatory condition and represents the most common of all superficial fungal skin infections. Over 1 million individuals in the U.S. contract Athlete's foot each year. It is predominantly caused by a group of fungi called dermatophytes which includes *Trichophyton rubrum*, *Trichophyton mentogrophytes* var. *interdigitale* and *Epidermophyton floccosum*. For most patients, recurrent or chronic foot fungal infections are more of an inconvenience than a problem and treatment is rarely sought. This may explain the high prevalence of the disease. Cellulitis is a more serious consequence of an untreated fugal foot infection. Although treatable, it can be a limb-threatening disease for patients with comorbidities. Individuals with diabetes have an increased risk of developing this complication. The frequent outcome for this group is hospitalization and an increased length of stay when compared to their non-diabetic counterparts.

There are three main groups of topical agents for treating fungal skin infections, allylamines (i.e. terbinafine), imidazoles (i.e. clotrimazole, ketoconazole, sulconazole and miconazole) and morpholine derivatives (i.e. amorolfine). All have been demonstrated to be more effective than placebo. However, their speed of action varies making compliance difficult and often resulting in ineffective treatment.

Alopecia, or hair loss, affects approximately 35 million men and 21 million women in the U.S. Alopecia areata is a disorder that causes sudden hair loss on the scalp and other regions of the body. It affects more than 5 million Americans, 60% of them under the age of 20. It is not a health threat, but can be psychologically damaging, especially for children, to cope with baldness. Of men being treated for alopecia, approximately 85% are being treated with Minoxidil and approximately 15% are being treated with Finasteride. Minoxidil, more commonly known as Rogaine™ is a nonprescription medication approved for androgenetic alopecia and alopecia areata. In a liquid or foam, it is rubbed into the scalp twice a day. This is the most effective method to treat male-pattern and female-pattern hair loss. However, only 30-40% of patients experience hair growth and it is not effective for other causes of hair loss. Hair regrowth can take 8 to 12 months and treatment must be continued indefinitely because hair loss resumes if treatment is stopped. Finasteride (Propecia™) is used in male-pattern hair loss in a pill form taken on a daily basis. It is not indicated for women and is not recommended in pregnant women. Treatment is effective within six to eight months of treatment. Side effects include decreased libido, erectile dysfunction, ejaculatory dysfunction, gynecomastia, and myopathy. Treatment should be continued as long as positive results occur. Once treatment is stopped, hair loss resumes. In 2013, it is anticipated that men will spend over $225 million on medicinal therapies like Rogaine™. Unfortunately, the low percentage of success, potential side effects and lifetime treatment regimen make this option difficult for many individuals.

Another particular area of concern involves foot or limb wounds in diabetic patients. It is known that foot wounds in diabetic patients represent a significant public health problem throughout the world. Diabetes is a large and growing problem in the U.S. and worldwide, costing an estimated $45 billion dollars to the U.S. health care system. Patients afflicted with diabetes often have elevated glucose and lipid levels due to inconsistent use of insulin, which can result in a damaged circulatory system and high cholesterol levels. Often, these conditions are accompanied by deteriorating sensation in the nerves of the foot. As a result, diabetics experience a high number of non-healing foot ulcers.

It is estimated that each year up to three million leg ulcers occur in patients in the U.S., including venous stasis ulcers, diabetic ulcers, ischemic leg ulcers, and pressure ulcers. The national cost of chronic wounds is estimated at $6 billion. Diabetic ulcers often progress to infections, osteomyelitis and gangrene, which often results in toe amputations, leg amputations, and in some cases death. In 1995, approximately 70,000 such amputations were performed at a cost of $23,000 per toe and $40,000 per limb. Many of these patients progress to multiple toe amputations and contralateral limb amputations. In addition, these patients are at an increased risk of heart disease and kidney failure from arteriosclerosis which attacks the entire circulatory system.

The conventional methods of treatment for non-healing diabetic ulcers include wound dressings of various types, antibiotics, wound healing growth factors, skin grafting including tissue engineered grafts, use of wheelchairs and crutches to remove mechanical pressure, and finally amputation. In the case of ischemic ulcers, surgical revascularization procedures via autografts and allografts and surgical laser revascularization have been applied with short term success, but with disappointing long term success due to reclogging of the grafts. In the treatment of patients with venous stasis ulcers and severe venous disease, antibiotics and thrombolytic anticoagulant and anti-aggregation drugs are often indicated. The lack of success of conventional methods is demonstrated by the failure to heal these wounds and their frequent recurrence. Accordingly, the medical community has a critical need for a low cost, portable, non-invasive method of treating diabetic, venous, ischemic and pressure ulcers to reduce mortality and morbidity and reduce the excessive costs to the health care system.

Most problematic of all is that treatment of diabetic foot ulcers has been focused on amputation and not on limb salvage primarily because the wounds have not been properly treated. Improper treatment can be attributed to lack of an easy and inexpensive treatment system and severe inconvenience to the patient in using current methods. There is a need to prevent amputation by healing such wounds, particularly at an early stage.

Furthermore, amputation for conditions such as foot ulcers and frostbite becomes less avoidable the longer the condition is either left untreated or is unsuccessfully treated. Therefore, it is crucial to apply an effective treatment regimen as soon as possible. Unfortunately, foot wounds in patients with, for example, diabetes develop because of a process called neuropathy. Diabetes causes loss of sensation such that skin injury and complete breakdown (ulcer) can develop with no or minimal pain. These wounds tend not to heal because of ongoing mechanical trauma not felt at all by the patient as painful. Therefore, by the time the patient discovers the wound, the wound has often progressed so that the patient's treatment options have become severely limited.

In many cases, such wounds can only be healed by protecting them from mechanical trauma. Small plantar ulcers in diabetic patients are usually seen by primary care practitioners and endocrinologists. The present method for healing plantar ulcers is a total contact cast for the foot, which provides complete mechanical protection. This method is not ideally suited for either of these practice settings, because it requires skilled and specialized care in application, along with frequent follow up. Most patients perceive the cast to be an inconvenience at the early stages of such a wound, while perceiving that such a wound is not a serious matter. The alternative to the cast is to have the patient use a wheelchair, crutches, or a walker, which can provide mechanical protection only with complete patient compliance. This alternative rarely proves to be effective in healing wounds within a reasonable time period.

Burn injuries affected approximately 450,000 individuals in 2013 according to The American Burn Association (www.ameriburn.org). Of these, approximately 40,000 resulted in hospitalization including 30,000 at hospital burn centers. Men (69%) were affected almost twice as much as women (31%). There are three burn classifications, first-degree burn, second-degree burn and third-degree burn. First degree burns are the least serious only involving the outer layer of skin. The skin is usually red, often swollen and painful. A second degree burn occurs when the second layer of skin (dermis) also is burned. When this occurs blisters develop, the skin has an intensely red splotchy appearance, swollen and very painful. In most circumstances, second degree burns no larger than three inches in diameter may be treated as a minor burn. Larger areas require immediate medical assistance. Treatment for minor burns including first-degree burns and limited area second-degree burns include: cooling the burn with cool running water for 10 or 15 minutes or until the pain subsides. This will reduce swelling by conducting heat away from the skin. Cover the burn with a sterile gauze bandage wrapped loosely about the affected area to avoid putting pressure on burned skin. Bandaging keeps air off the burn, reduces pain and protects blistered skin. Taking an over the counter pain reliever such as aspirin, ibuprofen, naproxen or acetaminophen can ease the discomfort. Minor burns usually heal without further treatment but often heal with significant pigment changes. However, continued redness, pain, swelling or oozing often indicates infection that can result in further damage, discoloration and disfigurement of the affected area.

Third degree burns are the most serious involving all layers of the skin and often include fat, muscle and some-times bone. Hospitalization is the best treatment for third degree burns. Discoloration and disfigurement often occur with third degree burns.

Consequently, there is a need in the wound treatment industry is a method for treating abrasions and lacerations of the skin, bacterial and fungal skin infections, hair loss, skin ulcers, burns and other wounds that does not require extended physician time and that is effective even at later stages of the medical condition. Also, what is needed is a treatment that allows patients to be able to continue their active lives without the need to wear casts, or be confined to wheelchairs and/or crutches.

SUMMARY

One aspect of the present invention is a portable variable hyperoxia treatment apparatus that comprises a housing containing a first, second and third sealable chambers, a programmable control circuit, a humidifier, a flow control regulator, a storage port, a main valve, an exit port and sealable caps for each of the chambers. The first sealable chamber is for housing an energy source. The second sealable chamber is for receiving a cartridge containing water or a medicament and the third chamber is for receiving a gas cartridge. Each chamber has a top and bottom ends. The programmable control circuit is powered by an energy source housed in the first sealable chamber. The humidifier is positioned at the top end of the second chamber, electronically connected to control circuit and in contact with water or a medicament in the chamber. A flow control regulator is positioned on the top end of the third chamber and electronically connected to the control circuit for dispensing gas from a gas cartridge. The storage port is located above the humidifier to house a humidified vapor or medicament. The main valve is in communication with the storage port and the flow control regulator and electronically connected to the control circuit. The exit port is in communication with the main valve for dispensing the humidified vapor or medicament.

In one embodiment of the present invention, the cartridge containing water or a medicament comprises a housing, an absorbent insert of a size that fits within the housing, and a compression spring that maintains the contact of the absorbent insert with the humidifier. The absorbent insert may be made of a variety of materials including natural or synthetic fiber.

In another embodiment, the humidifier is a piezoelectric disc that atomizes the water or medicament from the absorbent insert and deposits the atomized water or medicament into the storage port.

In yet another embodiment, the variable hyperoxia treatment apparatus further comprises one or more light emitting diodes or an adapter to connect one or more light emitting diodes electronically to the control panel. The light emitting diodes may emit infrared or ultraviolet light. Other elements of the apparatus may include a humidity sensor within the storage port and electronically connected to the control panel, and/or an oxygen sensor within the flow control regulator or the exit port and electronically connected to the control panel.

Another aspect of the present invention is a variable hyperoxia therapy treatment system comprises the portable variable hyperoxia apparatus described above and a treatment chamber for covering the treatment area in fluid connection with the exit port through a hollow tube. The treatment chamber may be affixed securely to a human body part or wherein a human body part may be inserted into the chamber for treatment. The treatment chamber may further comprise one or more light emitting diodes that emit infrared and/or ultraviolet light.

In other embodiments, the control circuit comprises a number of preprogrammed protocols configured to permit automatic operation of the system according to the protocol selected by the user. The control circuit may also be programmed by the user to create and store additional protocols. The apparatus may further comprise a wireless transmitter adapted to transmit data and/or a barcode data reader.

Another aspect of the invention is a method for treating a wound, comprising: (a) covering said wound with a treatment chamber; (b) surrounding the wound in said treatment chamber with a vapor containing water and/or a medicament; and (c) surrounding the wound in said treatment chamber with an $O_2$-enriched gas without increasing the pressure around the wound to 22 mm Hg wherein the vapor and $O_2$-enriched gas is prepared using a portable variable hyperoxia treatment apparatus disclosed above. The method may be used when the wound is a surgical incision, a chronic lesion, a post-surgical infection, a gangrenous lesion, a decubitus ulcer, a venous stasis, a skin ulceration due to amputation, skin graft, burn or frostbite. The medicament may be an antibiotic such as betadine, isopropyl alcohol, bacitracin, hydrogen peroxide, and combinations thereof. The antibiotic may also be ionic silver.

The method may be used when the wound is the result of bacterial infection, for example, acne specifically *Propionibacterium acnes*. For this condition, the medicament may be benzoyl peroxide, salicylic acid, glycolic acid, sulfur or azelaic acid.

The method may be used when the wound is the result of fungal infection, for example, Athlete's foot, specifically fungus of the genus *Trichophyton*. For this condition, the medicament may be (RS)-1-(2-(2,4-Dichlorobenzyloxy)-2-(2,4-dichlorophenypethyl)-1H-imidazole (Miconazole™), 1-[(2-chlorophenyl)(diphenyl)methyl]-1H-imidazole (Clotrimazole™), [(2E)-6,6-dimethylhept-2-en-4-yn-1-yl](methyl)(naphthalen-1-ylmethyl)amine (Terbinafine™), O-2-naphthyl methyl(3-methylphenyl)thiocarbamate (Tolnaftate™) or [(4-tert-butylphenyl)methyl](methyl)(naphthalen-1-ylmethyl)amine (Butenafine™).

Another aspect of the invention is a method for treating a medical condition, comprising: (a) covering said wound with a treatment chamber; (b) surrounding the wound in said treatment chamber with a vapor containing water and/or a medicament; and (c) surrounding the wound in said treatment chamber with an $O_2$-enriched gas without increasing the pressure around the wound to 22 mm Hg wherein the vapor and $O_2$-enriched gas is prepared using a portable variable hyperoxia treatment apparatus disclosed above.

The method may be used when the medical condition is a condition of the scalp such as alopecia. More specifically, alopecia areata or alopecia totalis. For this condition the medicament may be 6-piperidin-1-ylpyrimidine-2,4-diamine 3-oxide (Minoxidil™), N-(1,1-dimethylethyl)-3-oxo-(5α,17β)-4-azaandrost-1-ene-17-carboxamide (Finasteride™), (11β,16α)-9-fluoro-11,16,17,21-tetrahydroxypregna-1,4-diene-3,20-dione (Triamcinolone™), 17-hydroxy-7α-mercapto-3-oxo-17α-pregn-4-ene-21-carboxylic acid, γ-lactone acetate (Spironolactone™) or combinations thereof.

In other embodiments of these methods, the $O_2$-enriched gas may be substantially pure $O_2$. In other embodiments steps (b) and (c) are performed simultaneously or sequentially one or more times in a single treatment. For example, steps (b) and (c) may be performed simultaneously or separately for about 2 to about 30 minutes and preferably for approximately 15 minutes. In another embodiment, steps (b) and (c) are performed separately and step (c) is performed for approximately 5 minutes. In a preferred embodiment, steps (b) and (c) are performed 4 times either sequentially or simultaneously, the single treatment lasting approximately 80 minutes. The method may be repeated periodically until the wound is healed.

Other aspects of the invention are found throughout the specification.

DESCRIPTION OF DRAWINGS

These and other features and advantages will be apparent from the following more particular description thereof, presented in conjunction with the following drawings, wherein.

DETAILED DESCRIPTION

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "portable" as used herein refers to the ability of the apparatus to be easily transported from one location to the other by the user because of its small size and light weight. This term is also used to refer to the apparatus being transportable, mobile and/or wearable.

The term "cartridge" as used herein refers to a holding cylinder for the absorbent insert. The cartridge may have a number of configurations that achieve this goal. The cartridge is preferably disposable and may have a spring that applies pressure to keep the absorbent insert up against the humidifier. Correspondingly, the cartridge may hold the absorbent insert tightly with a part of the insert extending beyond the end of the cartridge. In this configuration the cartridge may have a twisting compression lock maintaining contact of the absorbent insert with the humidifier when the cartridge is twist locked in place.

The term "programmable control circuit" as used herein refers to the circuitry that operates the apparatus. The control circuit includes a computer processing unit with memory, preprogrammed protocols that may be selected from a menu, provides a user interface that allows the user to program and save additional protocols as well as controlling the functions of the humidifier, flow control regulator, main valve, light emitting diodes, humidity sensor and oxygen sensor and activating or deactivating any or all of these elements based on the protocol selected by the user.

The term "medicament" as used herein refers to a solution of a compound or compounds that provide a therapeutic effect to the treatment area including antibacterial agents, antifungal agents, antiseptics, wound healing agents and medicinal agents.

The "absorbent insert" as used herein is a natural or synthetic fiber that is able to absorb a fluid and provide that fluid to the humidifier. The fiber is preferably bidirectional or unidirectional allowing the fluid to migrate via capillary action to the humidifier for vaporing the fluid.

The apparatus, treatment systems, and methods described herein provide hyperbaric oxygen and a humidified medicament as therapy in wound management and treatment. In addition, the described apparatus, systems, and methods, may also provide the application of antibacterial agents as well as infrared and ultraviolet light therapy to promote healing and suppression of bacterial growth.

Figure 1:
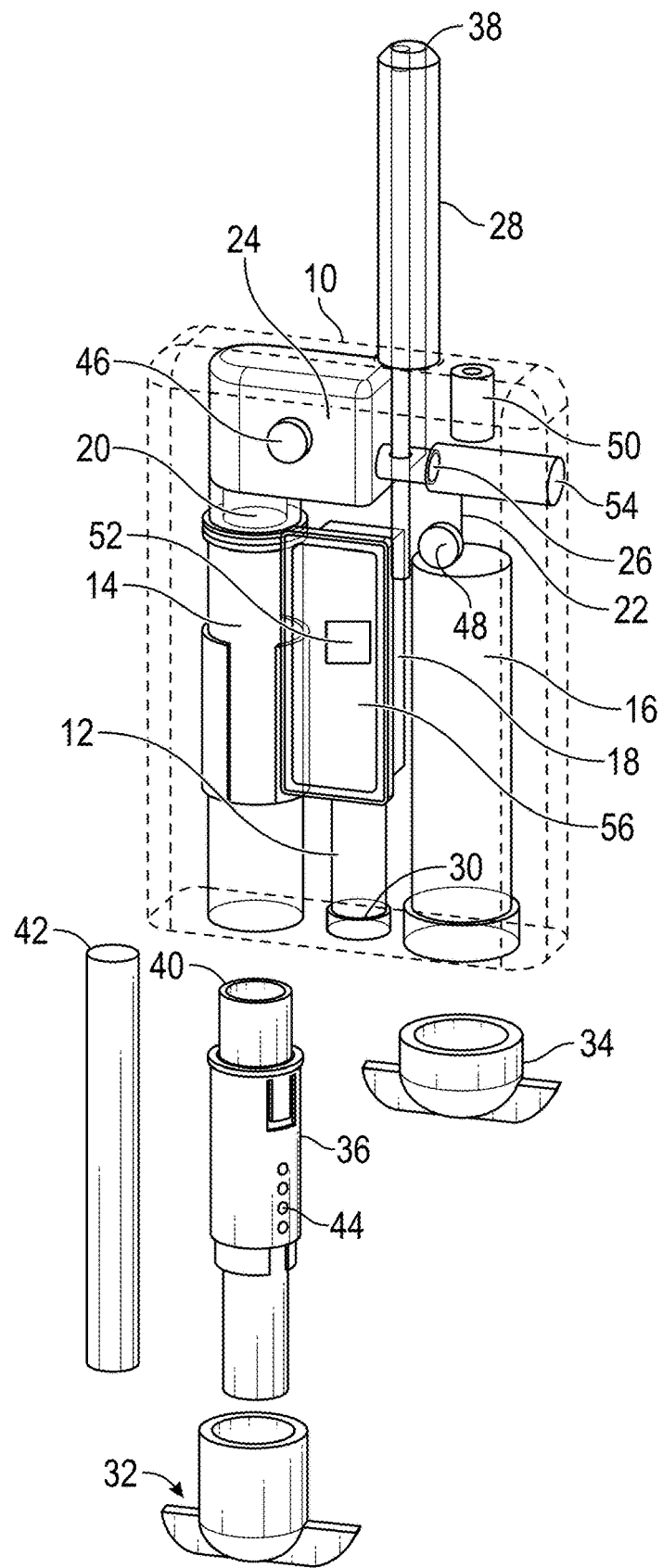
FIG. 1 is a perspective view of a portable variable hyperoxia treatment apparatus of the present invention.
Figure 2:
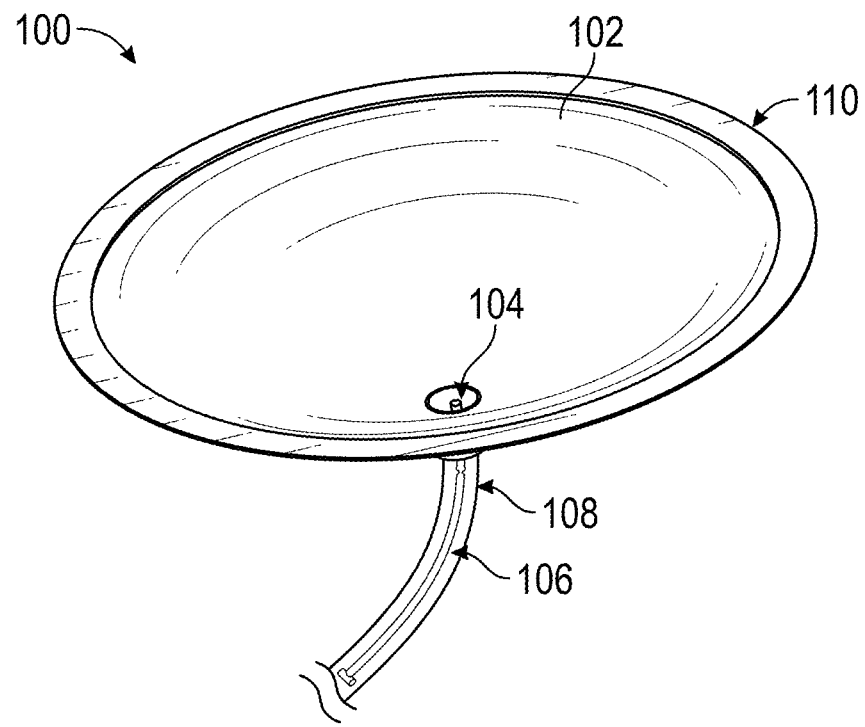
FIG. 2 is an illustration of a disposable treatment chamber for use with the methods and apparatus of the present invention.
Figure 2:
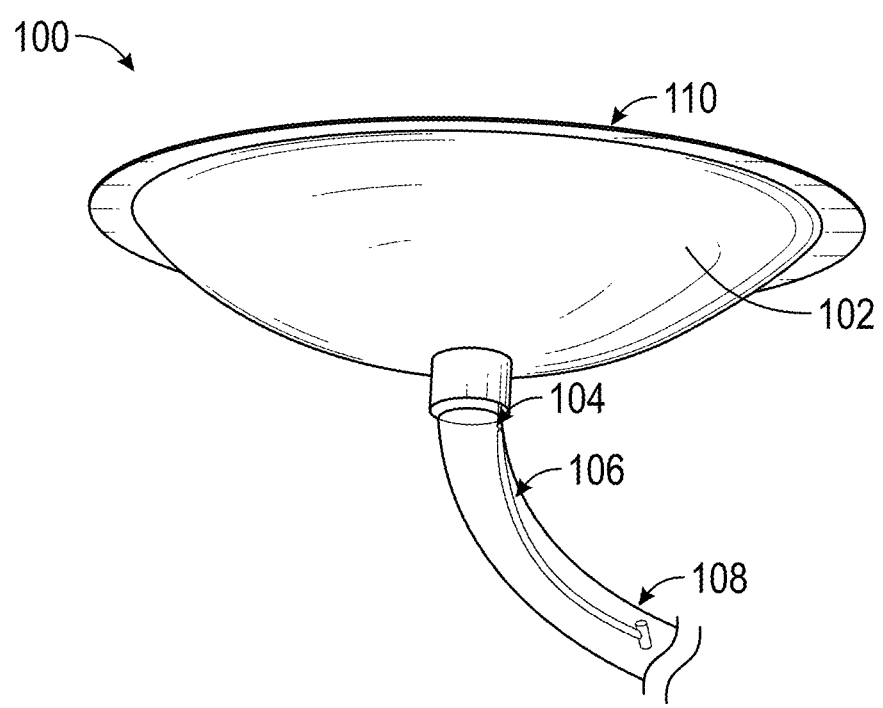

Turning to FIG. 1, a portable variable hyperoxia treatment apparatus 10 is shown, which prepares and dispenses a humidified medicament and an oxygen enriched gas simultaneously or sequentially at a pressure slightly greater than atmospheric pressure to a wound encased by a treatment chamber. The apparatus generally includes a housing having three sealable chambers 12, 14 and 16, a programmable control circuit 18, a humidifier 20, a flow control regulator 22, a storage port 24, a main valve 26, an exit port 28 and sealable caps 30, 32 and 34 for each of the chambers. The first sealable chamber 12 is for housing an energy source. The second sealable chamber 14 is for receiving a cartridge 36 containing water or a medicament and the third chamber 16 is for receiving a gas cartridge. Each chamber has a top and bottom ends. The programmable control circuit 18 is powered by an energy source housed in the first sealable chamber 12. The humidifier 20 is positioned at the top end of the second chamber 14, electronically connected to the programmable control circuit 18 and in contact with water or a medicament in the chamber. A flow control regulator 22 is positioned on the top end of the third chamber 16 and electronically connected to the control circuit 18 for dispensing gas from a gas cartridge. The storage port 24 is located above the humidifier 20 to house humidified vapor or medicament. The main valve 26 is in communication with the storage port 24 and the flow control regulator 22 and electronically connected to the control circuit 18. The exit port 28 is in communication with the main valve 26 for dispensing the humidified vapor or medicament. The entire apparatus is of a size that can be easily transported or stationed on a table or counter top for treatment administration.

The first chamber 12 is provided in a size sufficient to house an energy source such as a battery. The size of the chamber may vary depending on the dimensions of the battery based on the energy requirement of the programmable control circuit 18. The chamber will allow for easy access to the energy source for replacement. When the cap 30 is in place the circuit servicing the programmable control circuit 18 is complete energizing the apparatus 10. The cap 30 may have a moisture resistant seal to prevent damage to the apparatus circuitry from water.

The second chamber 14 is provided in sufficient size to house a cartridge 36 containing water or a medicament. The cartridge 36 may be provided in a variety of configurations. In one embodiment, the cartridge 36 comprises a hollow cylindrical sleeve 40 that houses a cylindrical absorbent insert 42 saturated with water or a medicament. In one preferred embodiment the housing further comprises a spring 44 that tensions the absorbent insert 42 against the top end of the chamber during use. In one configuration the spring 44 is provided on the base of the hollow cylindrical sleeve 40 so that when the cap 32 is in place the spring 44 is compressed exerting force on the sleeve 40 pressing the absorbent insert 42 against the top end of the chamber 14. In this configuration the cartridge 36 may be easily extracted from the apparatus 10 and easily replaced or the cartridge 36 reused and the absorbent insert 42 replaced. The cap 32 may have a moisture resistant seal to prevent damage to the control circuit from water. In a preferred embodiment the absorbent insert 42 is a unidirectional matrix in which capillary action allows the water or medicament contained in the matrix to travel to the humidifier during use.

The cartridge 36 may contain water or a variety of medicaments depending on the condition being treated. For example, an antibacterial agent, such as ionic silver, hydrogen peroxide, bacitracin, betadine, or isopropyl alcohol may be used for open wounds such as laceration, cuts or surgical incisions. In one embodiment, humidified 1% hydrogen peroxide/silver solution is used. If the condition being treated is fungal, the medicament may be for example (RS)-1-(2-(2,4-Dichlorobenzyloxy)-2-(2,4-dichlorophenypethyl)-1H-imidazol e (Miconazole™), 1-[(2-chlorophenyl)(diphenyl)methyl]-1H-imidazole (Clotrimazole™), [(2E)-6,6-dimethylhept-2-en-4-yn-1-yl](methyl)(naphthalen-1-ylmethyl)amine (Terbinafine™), O-2-naphthyl methyl(3-methylphenyl)thiocarbamate (Tolnaftate™) or [(4-tert-butylphenyl)methyl](methyl)(naphthalen-1-ylmethyl)amine (Butenafine™). If the condition being treated is acne, the medicament may be for example benzoyl peroxide, salicylic acid, glycolic acid, sulfur or azelaic acid. For treatment of alopecia, the medicament may be 6-piperidin-1-ylpyrimidine-2,4-diamine 3-oxide (Minoxidil™), N-(1,1-dimethylethyl)-3-oxo-(5α,17β)-4-azaandrost-1-ene-17-carboxamide (Finasteride™), (11β,16α)-9-fluoro-11,16,17,21-tetrahydroxypregna-1,4-diene-3,20-dione (Triamcinolone™), 17-hydroxy-7α-mercapto-3-oxo-17α-pregn-4-ene-21-carboxylic acid, γ-lactone acetate (Spironolactone™) or combinations thereof. In other embodiments, FDA approved topical antibacterial, antibiotic, antiseptics and antimicrobial solutions and agents, may also be used.

A humidifier is located at the top end of chamber 14 in direct contact with the absorbent insert 42. In one embodiment, the humidifier 20 is a piezo-electric disc electronically connected to the programmable control circuit 18. When the piezo-electric disc is activated is vaporizes the fluid supplied by the absorbent insert 42 through sound vibrations. Capillary action in the absorbent insert 42 will maintain fluid at the humidifier 20 interface allowing continued production of vapor. On the other side of the humidifier 20 is the storage port 24 where the vapor is stored before be applied to the wound treatment area. The absorbent insert 42 may be made of any material that allows fluid contained in the insert 42 to wick in a desired direction based on capillary action. For example, the absorbent insert 42 may be a natural fiber such as cotton or a hard felt made of rayon a semi-synthetic fiber or cellulose acetate a synthetic fiber. In another embodiment of the present invention, the piezo-electric disc may provide a dual purpose of vaporizing the fluid supplied by the absorbent insert 42 as well as providing a low intensity ultrasound frequency, such as for example between 20 KHz and 100 kHz applied to the treatment area for about 15 to about 45 minutes. Low intensity ultrasound frequencies such as these have been shown to improve chronic wound healing (C. Schultz, Expose Wounds to the Right Kinds of Sound, and They Heal Faster, Drexel University, College of Medicine, January 2014, Smithsonianmag.com).

The humidifier 20 has a transducer that generates ultrasonic energy at about 40 kHz to create an adiabatic/humid vapor that creates a cloud. When the main valve 26 is opened, the vapor travels from the storage port 24 into the exit port 28 where it enters the hollow tubing 108 that leads to the treatment chamber 102 secured over the treatment area.

The third chamber 16 is provided in sufficient size to receive a small gas cartridge similar in size to a standard $CO_2$ cartridge but instead containing oxygen. At the top end of the chamber 16 is a seat to receive the top of the gas cartridge. At or about the center of the seat is a puncture pin and flow control regulator 22 connected electronically to the programmable control circuit 18. When the cap 34 is tightened sealing the third chamber 16, force is applied to the gas cartridge pressing the gas cartridge plug against the pin puncturing the plug and allowing gas to flow into the flow control regulator 22. The cap 34 may have a moisture resistant seal to prevent damage to the apparatus circuitry from water.

The programmable control circuit 18 provides an interactive display that allows the user to select programmed protocols from a menu to meet the treatment requirements. These protocols may be preprogrammed into the control circuit memory when purchased or they may be programmed by the user and stored in the control circuit memory. The control circuit 18 regulates the vaporization of the water or medicament supplied by the absorbent insert 42, the flow rate of oxygen from the gas cartridge, the sequential or simultaneous application of the humidified medicament and oxygen, the dispensing rate of the humidified medicament, oxygen or mixture of both and the emission of infrared and/or ultraviolet light to the affected area.

The dispensing of the humidified medicament or vaporized water and oxygen are regulated by the main valve 26, which is electronically controlled by the programmable control circuit 18. The main valve 26 is preferably a three way valve that can allow only humidified medicament, only oxygen or a combination of both to be dispensed to the affected area through the exit port 28. In conjunction with the dispensing of oxygen and humidified medicament the programmable control circuit 18 will also control the emission of infrared and/or ultraviolet light through one or more light emitting diodes 38 on the tip of the exit port 28 or built into the treatment chamber 100 that covers the treatment area.

A wide variety of treatment chamber 100 configurations may be utilized with the portable variable hyperoxia treatment system based on the location and size of the area being treated. In each case, the treatment chamber 102 will be connected to the apparatus 10 through a hollow tube 108 affixed to the exit port 28 of the apparatus 10. The treatment chamber 102 will be made of an impermeable flexible polymer that will retain the humidified medicament in contact with the affected area. The treatment chamber 102 may be provided in a configuration that will encase an appendage such as a finger or hand having a means for securing the open end about the appendage. This means of attachment may be a physical means such as a draw string or by chemical means such as the use of an adhesive. In another configuration, the treatment chamber 102 may be shaped like a dome with adhesive along the edges 110 so that the chamber 102 may be easily affixed on a relatively flat area such as the chest or back of the user. In either configuration, the hollow tube 108 providing the humidified medicament to the affected area may be located around or about the center of the treatment chamber 102 or off the side. The treatment chamber 102 may have a release valve (not shown in the drawings) that allows the humidified gas inside the chamber 102 to escape once a desired pressure is reached.

In one embodiment, a set of light emitting diodes that generate infrared and/or ultraviolet light 104 are provided on or within the treatment chamber 102 and electrically connected to the programmable control circuit 18. This electrical connection may be established directly when the hollow tubing 108 of the treatment chamber 100 is connected to the exit port 28 or may require that the user make the connection by plugging the light emitting diode wire 106 into a jack 50 provided on the apparatus 10 that connects the LEDs to the programmable control circuit 18. In another embodiment, a light emitting diodes 38 is provided in the tip of the exit port 28 and electronically connected to the control circuit 18.

The storage chamber 24 may further comprise a humidity sensor 46 electronically connected to the programmable control circuit 18 to monitor the vapor in the chamber and to assure that the components of chamber 2 are operating appropriately. For example, if the vapor in the chamber is insufficient it may indicate that sufficient fluid is not available in the absorbent insert, the insert may not be in sufficient contact with the humidifier 20 or the humidifier 20 may not be functioning properly.

In addition, the apparatus 10 may further comprise an oxygen sensor 48, a wireless transmitter 52 and/or a bar code reader 54. The oxygen sensor 48 is in contact with the flow control regulator 22 to assure that adequate oxygen is being provided according to the selected or programmed protocol and to determine whether the oxygen cartridge should be replaced. The wireless transmitter 52 may transmit data to a local desk top computer, a cell phone, a tablet or other similar device or may transmit the data over the internet, phone line or to a cloud where medical personnel can review the data. A bar code reader 54 may be provided to read a bar code on prepared medicament cartridges 36 before use to assure that the appropriate medicament is being applied and to record the date of treatments as well as protocols used with that medicament cartridge 36.

In operation, the apparatus 10 works by switching the master power switch to the on position, which turns the system on and puts the system in ready mode. The user then selects which of the protocols existing in the control circuit 18 to be used or whether a new protocol will be programmed. Depending on the condition to be treated, the protocol selected may provide for operation of all, or just some, of the functions. For example, a protocol may call for treating the affected area with the antibiotic vapor, but may not require infrared or ultraviolet treatment. The control circuit screen 56 will provide options that the user may select in deciding on the appropriate protocol for treatment or to allow the user to program a new protocol. Establishing these types of menu selections is well known in the art and can be easily programmed into the control circuit 18. When a specific protocol is selected the apparatus will provide a prompt to the user to initiate treatment when the user is ready. According to one embodiment, the vapor may be set at about fifteen minutes, the oxygen set at about five minutes, the IR illumination set at about one to about ten minutes and the UV illumination set at less than 5 seconds, less than 4 seconds, less than 3 seconds, less than 2 seconds, or less than 1 second.

In one example of using the apparatus 10, the affected area of the user is first cleaned. The user selects a protocol from the menu items displayed on the control circuit screen 56. The treatment chamber 100 that is substantially impermeable to gas is then applied over the affected area. The treatment chamber 102 is secured in place by adhesive along the chambers perimeter edge. Once secured the start button is pressed and the apparatus initiates the selected treatment protocol. An exemplary protocol may begin with activation of the UV LED(s) 104 of the treatment chamber through the light emitting diode wire 106 to the control circuit 18. The LTV LED(s) 104 briefly stimulate the affected area (about one to five seconds). The array of IR LEDs in the treatment chamber is then activated transmitting a pulsed (or steady) IR light that warms the limb increasing circulation. A humidified vapor of water and/or a topical antibacterial, antiseptic or antibiotic agent in water is released from the humidifier and maintained in the storage port 24. The humidified vapor is released independently or simultaneously with oxygen through the main valve 26 into the exit port 28 and travels through the hollow tubing 108 to the treatment chamber 102. In one embodiment, vapor treatment lasts about fifteen minutes.

Under certain protocols the humidified vapor and oxygen are released sequentially. For example, in one protocol the main valve 26 releases the humidified vapor first for a given treatment period followed by release of oxygen. The oxygen displaces the vapor and oxygenates the wound. Oxygenation can last between about one minute and about fifteen minutes. In one embodiment, oxygenation lasts about five minutes. The process between vapor treatment and oxygenation can be repeated several times. In one embodiment, vapor treatment and oxygenation are repeated three times for a total of four rounds of treatment lasting approximately eighty minutes.

In one embodiment, there can be as few as one LED and as many as twenty or more LEDs in the array of UV and/or IR LEDs. The array of UV LEDs 38 can deliver 330 W of UVA at about 320 nm to about 400 nm. Alternatively, or in addition to, the array of UV LEDs can deliver 330 W of UVB at about 290 nm to about 320 nm. Alternatively, or in addition to, the array of UV LEDs can deliver 330 W of UVC at about 100 nm to about 200 nm. In one embodiment, there are twenty UV LEDs delivering 330 W of UVA at about 374 nm to about 392 nm, delivering a total of about 324 mW or 324 W.

The IR LEDs 38/104 can emit energy at infrared frequencies of between about 700 nm and 50,000 nm. The frequency at which the IR LEDs emit may be controlled by the control circuit 18. In one embodiment, the IR LEDs deliver about 2000 mW of infrared light at about 810 nm. In one embodiment, the IR LEDs can also generate about 1.2 W of Red light at about 660 nm for a combined total light output of 1911 mW. In one example, the LEDs may be a Thor DDII IR Lamp System.

There is only one component of the wound treatment system that makes physical contact with the patient's skin: that is the treatment chamber 102, which is secured around the treatment area. The treatment chamber 102 forms a treatment zone around the wound and makes contact with the open wound. Therefore, it is preferable that the treatment chamber 102 be biocompatible and sterile and preferably disposable.

The material from which the treatment chamber 102 is made can be any strong substantially gas impermeable material. Extruded flexible plastic film material, such as polyethylene (hdpe, ldpe, lldpe, polyprolene, etc), polyurethane ether or ester open cell foam (e.g., United States Plastics Corp. Stock No. 47154), polyethylene terephthalate, polyvinyl chloride, or ethylene/polyvinyl copolymer sheet stock, and vapor proof treated fabric, such as nylon, are suitable. The material can be puncture resistant and transparent. The flexible sheet material can have a variety of shapes. It can be a single layer or have multiple layers.

The term "substantially gas impermeable", as used herein with respect to the sheet material, means gas impermeable to the extent needed to prevent excessive gas escape from the treatment zone through the sheet material. Total gas impermeability seldom is needed, particularly for continuous flow treatment devices. However, generally high impermeability is desirable for static treatment devices.

The perimeter of the opening of the treatment chamber 102 can have an adhesive strip 110 with a removable backing. The backing can be removed and the perimeter of the lining can be substantially sealed against the skin around the treatment area, thus forming a sealed connection between the perimeter of the treatment chamber 102 and the affected area. Alternatively, the treatment chamber 102 may have a draw string allowing the chamber to be secured about an appendage such as a finger or hand.

In one embodiment, the treatment chamber 102 includes a pressure release valve. The design of the pressure release valve is not critical. Many different types are suitable. For example, the valve can be a ball valve or a baffle valve such as a flap or butterfly baffle valve. Other valves are equally suitable, so long as they are capable of accurately setting the maximum release pressure and are inexpensive and so disposable. In one embodiment, the maximum release pressure can be set at 22 mm of mercury so that the pressure inside the treatment chamber 102 never surpasses that amount of pressure. The valve body can be made of any rigid plastic, although metals such as stainless steel may also be used. Inexpensive valves made completely of plastic may be used as well.

The disclosure set forth above is provided to give those of ordinary skill in the art a complete disclosure and description of how to make and use embodiments of the compositions and methods of the present invention, and are not intended to limit the scope of what the inventors regard as their invention. Modifications of the above-described modes (for carrying out the invention that are obvious to persons of skill in the art) are intended to be within the scope of the following claims. All publications, patents, and patent applications cited in this specification are incorporated herein by reference in their entirety as if each such publication, patent or patent application were specifically and individually indicated to be incorporated herein by reference.

What is claimed is:

1. A portable variable hyperoxia treatment system, comprising:
    a housing comprising:
        a programmable control circuit powered by an energy source;
        a humidifier in fluid communication with a fluid source containing a fluid, the humidifier configured to generate a humidified vapor, wherein the humidifier comprises a piezo-electric disc configured to vaporize the fluid from an absorbent insert;
        a gas source containing a gas;
        a flow control regulator connected to the control circuit for dispensing gas from the gas source;
        a main valve controlled by the control circuit and connected to the humidifier and the flow control regulator; and
        an exit port connected to the main valve for dispensing said humidified vapor and gas; and
    a treatment chamber configured to configured to cover a treatment area, the treatment chamber in fluid communication with the exit port through hollow tubing.

2. The portable hyperoxia therapy treatment system of claim 1, wherein the treatment chamber is configured to be affixed to a human body part or wherein a human body part may be inserted into the chamber for treatment.

3. The portable hyperoxia therapy treatment system of claim 1, wherein the treatment chamber comprises one or more light emitting diodes having a connector for electronically connecting the light emitting wherein the treatment chamber is not contained within the housing.

4. The portable hyperoxia therapy treatment system of claim 3, wherein the light emitting diodes emit IR and/or UV light.

5. The portable hyperoxia therapy treatment system of claim 1, wherein the control circuit comprises one or more protocols stored in the control circuit to permit automatic operation of the system of a selected protocol.

6. The portable hyperoxia therapy treatment system of claim 5, wherein at least one of the one or more protocols are configured to alternatingly surround the treatment area with the humidified vapor and the gas.

7. The portable hyperoxia therapy treatment system of claim 1, further comprising a wireless transmitter adapted to transmit data.

8. The portable hyperoxia therapy treatment system of claim 1, wherein the piezo-electric disc emits low intensity ultrasound frequencies between about 20 kHz to about 100 kHz.

9. The portable hyperoxia therapy treatment system of claim 1, wherein the gas comprises oxygen.

10. The portable hyperoxia therapy treatment system of claim 1, wherein the fluid comprises water.

11. The portable hyperoxia therapy treatment system of claim 1, wherein the medicament comprises an antibiotic selected from the group consisting of isopropyl alcohol, bacitracin, hydrogen peroxide, and combinations thereof.

12. The portable hyperoxia therapy treatment system of claim 1, wherein the medicament comprises ionic silver.

13. The portable hyperoxia therapy treatment system of claim 1, wherein the treatment chamber comprises an opening and a drawstring configured to close the opening around the human body part.

14. The portable hyperoxia therapy treatment system of claim 1, wherein the treatment chamber comprises an opening and an adhesive configured to seal the opening around the human body part.

15. The portable hyperoxia therapy treatment system of claim 1, wherein the treatment chamber comprises an impermeable flexible polymer.

16. The portable hyperoxia therapy treatment system of claim 1, wherein the treatment chamber comprises a release valve.

17. The portable hyperoxia therapy treatment system of claim 1, wherein the hollow tubing is flexible such that a position of the treatment chamber can be adjusted relative to a position of the housing.

* * * * *